United States Patent
Kronmueller et al.

(10) Patent No.: US 11,129,995 B2
(45) Date of Patent: Sep. 28, 2021

(54) OUTER CASING PART OF AN IMPLANTABLE MEDICAL ELECTRONIC DEVICE

(71) Applicant: BIOTRONIK SE & CO. KG, Berlin (DE)

(72) Inventors: Daniel Kronmueller, Nuremberg (DE); Thomas Sontheimer, Rosstal (DE)

(73) Assignee: BIOTRONIK SE & Co. KG, Berlin (DE)

( * ) Notice: Subject to any disclaimer, the term of this patent is extended or adjusted under 35 U.S.C. 154(b) by 305 days.

(21) Appl. No.: 16/133,764

(22) Filed: Sep. 18, 2018

(65) Prior Publication Data

US 2019/0099603 A1 Apr. 4, 2019

(30) Foreign Application Priority Data

Sep. 29, 2017 (EP) .................................... 17193996

(51) Int. Cl.
  *A61N 1/375* (2006.01)
  *A61N 1/08* (2006.01)
  *A61N 1/37* (2006.01)
  *A61N 1/36* (2006.01)
  *A61N 1/362* (2006.01)

(52) U.S. Cl.
  CPC .............. *A61N 1/375* (2013.01); *A61N 1/08* (2013.01); *A61N 1/362* (2013.01); *A61N 1/3605* (2013.01); *A61N 1/36038* (2017.08); *A61N 1/3718* (2013.01); *A61N 1/37512* (2017.08)

(58) Field of Classification Search
  CPC ................ A61N 1/375; A61N 1/36038; A61N 1/37512; A61N 1/08; A61N 1/3605; A61N 1/362; A61N 1/3718
  See application file for complete search history.

(56) References Cited

U.S. PATENT DOCUMENTS

| | | | |
|---|---|---|---|
| 5,714,103 A | 2/1998 | Bauer et al. | |
| 7,551,963 B2 | 6/2009 | Rusin et al. | |
| 8,536,468 B2 | 9/2013 | Teske | |
| 8,718,774 B2* | 5/2014 | Knipfer | A61N 1/37512 607/36 |
| 2008/0051854 A1* | 2/2008 | Bulkes | A61N 1/37211 607/60 |
| 2010/0274309 A1 | 10/2010 | Knipfer et al. | |
| 2012/0194981 A1* | 8/2012 | Kempf | A61N 1/37512 361/679.01 |
| 2015/0314131 A1* | 11/2015 | Stevenson | H01R 43/00 174/650 |
| 2016/0121599 A1 | 5/2016 | Bauer | |

(Continued)

FOREIGN PATENT DOCUMENTS

| | | |
|---|---|---|
| EP | 1685874 A1 | 8/2006 |
| EP | 2371418 A2 | 10/2011 |

(Continued)

*Primary Examiner* — Pete T Lee
(74) *Attorney, Agent, or Firm* — Laurence A. Greenberg; Werner H. Sterner; Ralph E. Locher

(57) ABSTRACT

A metal outer casing part of an implantable medical electronic device contains at least one inner cavity and/or non-conductive inclusion or portion with multiple small cavities and/or non-conductive inclusions which is closed off in a hermetically sealed manner at least towards the housing outer side by a closed metal layer.

18 Claims, 3 Drawing Sheets

(56) References Cited

U.S. PATENT DOCUMENTS

2016/0271399 A1 9/2016 Starke
2017/0203105 A1 7/2017 Sontheimer et al.

FOREIGN PATENT DOCUMENTS

| EP | 3069757 A1 | 9/2016 |
| EP | 3195899 A1 | 7/2017 |
| WO | 9316865 A1 | 9/1993 |
| WO | 2014187567 A2 | 11/2014 |

* cited by examiner

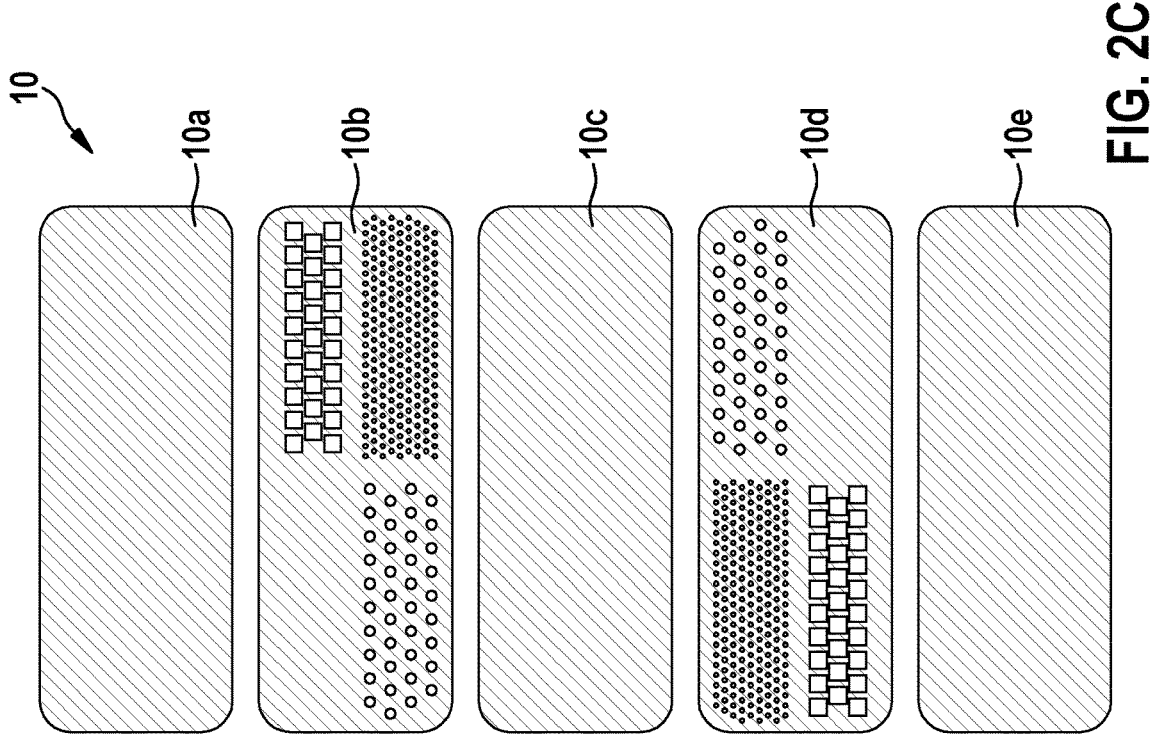
FIG. 2C
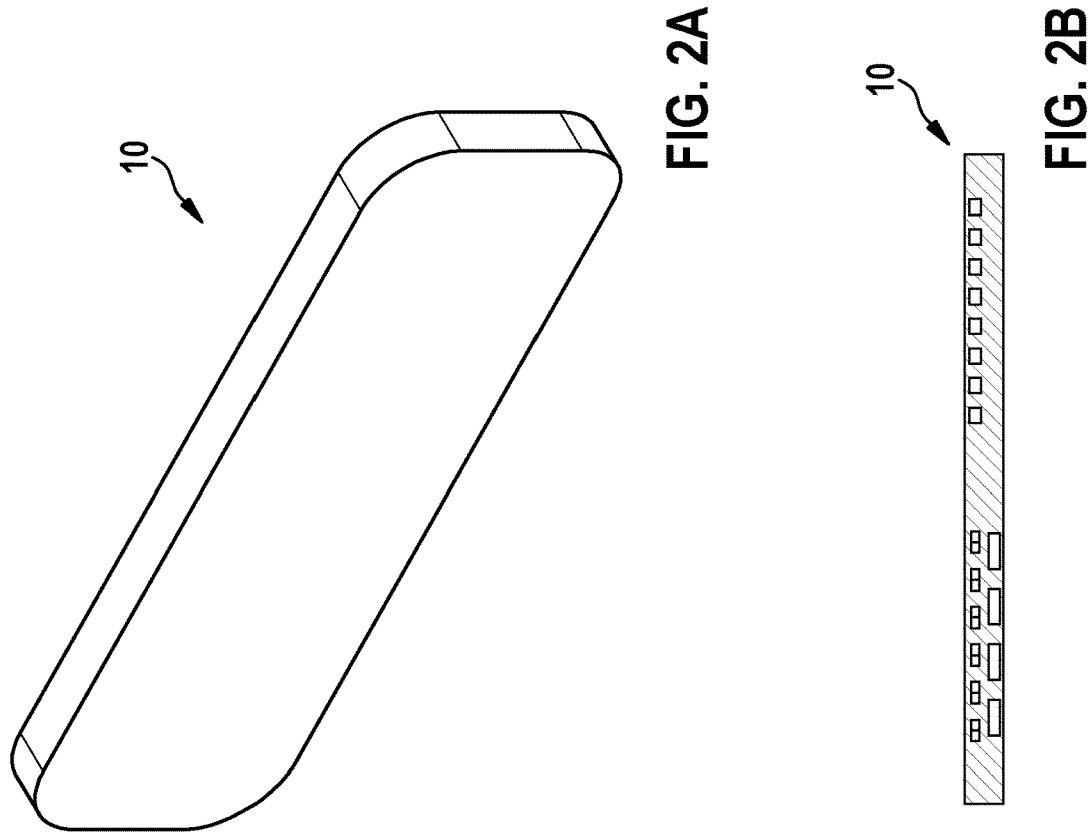
FIG. 2A
FIG. 2B

OUTER CASING PART OF AN IMPLANTABLE MEDICAL ELECTRONIC DEVICE

CROSS-REFERENCE TO RELATED APPLICATION

This application claims the priority, under 35 U.S.C. § 119, of German application EP 17193996.0, filed Sep. 29, 2017; the prior application is herewith incorporated by reference in its entirety.

BACKGROUND OF THE INVENTION

Field of the Invention

The invention relates to a metal outer casing part of an implantable medical electronic device. In particular, the invention relates to a feedthrough flange of a device of this kind or the housing half-shells, which in the joined state form the outer casing of the medical electronic device. The invention also relates to a medical electronic device itself, in particular a cardiac pacemaker or cardioverter or a cochlear implant or a neurostimulator.

Implantable medical electronic devices, such as cardiac pacemakers or implantable defibrillators, have long been known and used on a mass scale for the treatment of disturbances in heart rhythm. In recent years, new implantable devices, such as neurostimulators or cochlear implants, have also enjoyed widespread use. Such devices typically have a metal outer casing, which must be hermetically sealed, and electrical and electronic functional units inside the device which must be permanently protected against bodily fluids. At the same time, an outer casing of this kind offers protection against electromagnetic interference (EMI) from the living environment of the patient or during imaging processes for diagnosis.

Most implantable medical electronic devices of practical importance are intended to measure signals of the body via suitable sensors or to actively stimulate nerves and/or tissue. In order to perform this function, electronic/electrical functional units for processing data and/or for suitably controlling the stimulus generation are accommodated in the housing of the device. The sensors are often connected outside the medical electronic device via at least one electrode lead.

So that the patient is not hindered as a result of having to wear the implant, the electronic/electrical functional units are encapsulated by a biocompatible, hermetically sealed outer casing. On the one hand, this prevents the organism from attacking or resorbing materials of the electronics and thus gradually becoming poisoned by heavy metals, such as lead or copper. On the other hand, the hermetic encapsulation prevents the electronics from being damaged by liquids of the organism and thus losing their functional capabilities. The outer casing is joined from a number of parts. These are often housing half-shells, which are supplemented as required by electrical feedthroughs and/or what is known as a header.

The hermeticity is examined on the basis of the leak rate, which can be determined for example by leak tests. Appropriate leak tests can be performed for example using helium leak testers and/or mass spectrometers and are specified in the standard Mil-STD-883G Method 1014. The maximum permissible helium leak rate is defined there depending on the internal volume of the device to be tested. In accordance with the methods specified in Mil-STD-883G Method 1014 in paragraph 3.1, and under consideration of the volumes and cavities of the devices to be tested provided in the application of the present invention, these maximum permissible helium leak rates are for example from $1\times10^{-8}$ mbar·L/sec to $1\times10^{-7}$ mbar·L/sec.

Within the scope of the invention the term "hermetically" can mean in particular that the device to be tested (for example the housing and/or the electric feedthrough or the housing with the electric feedthrough) has a helium leak rate of less than $1\times10^{-7}$ mbar·L/sec. In an advantageous embodiment the helium leak rate can be less than $1\times10^{-9}$ mbar·L/sec, in particular less than $1\times10^{-10}$ mbar·L/sec.

The mentioned housing half-shells usually consist of a metal (for example of titanium Grade 1, titanium Grade 2, titanium Grade 3, 316L, molybdenum Grade 2, or the like). This ensures very good electromagnetic shielding and protects the sensitive electronics against magnetic fields and electromagnetic radiation. The electronics can also be encapsulated by means of resins or other plastics materials. The task of keeping electrical and/or magnetic fields away from the printed circuit board or, conversely, protecting the surrounding environment against the fields emanating from the medical device must then be taken into consideration when designing the printed circuit board and selecting the components. In the case of medical electronic devices having external sensors or electrodes, the housing half-shells are additionally joined with an electrical feedthrough. The feedthrough enables the exchange of electrical signals from inside the housing to outside the housing by means of the connection joined in a hermetically sealed manner.

In the case of devices such as cardiac pacemakers or implantable cardioverters, a feature of this kind generally consists of a solid metal feedthrough flange, which for example is milled from titanium, and an insulating body or a plurality of insulating bodies inserted therein, with connection pins in turn being embedded in the insulating body/bodies. The solid feedthrough flange has a rather high weight relative to the weight of other essential components of the device.

The function and production of a medical feature of this kind are the subject of numerous patent publications (for example EP 2 371 418 A2, EP 1 685 874 A1 corresponding to U.S. Pat. Nos. 8,536,468 and 7,551,963 respectively) and are therefore presupposed as being known and will not be described in greater detail.

In the interest of high wearing comfort and a resultant favourable, high level of acceptance by users, a device of the above-mentioned kind should be as lightweight as possible. Since there is only limited potential for weight savings in respect of the electrical and electronic functional units, there is a need for device housings and feedthroughs that are as lightweight as possible.

For the outer casing, consisting of housing half-shells and flange of the electrical feedthrough, the described devices on the whole are also subject to the requirement that they on the one hand protect the functional units received in the housing as reliably as possible against the influence of heavy static and high-frequency magnetic fields in the event that the patient undergoes magnetic resonance examinations (MRI), and on the other hand permit minimal interference during the examinations. In particular, where possible the components should not heat up when exposed to strong magnetic fields or should only heat up very slightly.

These essential aspects are described in the MRI safety test for medical implants and instruments according to standard ASTM F2182 "Standard Test Method for Measurement of Radio Frequency Induced Heating On or Near Passive Implants During Magnetic Resonance Imaging". It is thus necessary, for the approval of medical devices, to limit the heating of the tissue to a permissible value. Since the signal-noise ratio is better with greater field strengths, diagnosis is based increasingly on ultra-high field magnetic resonance tomography with more than 3T field strength. In order to enable advances in imaging examination also for patients having implants, the implant must be designed such that the eddy currents in the outer casing are as small as possible and/or the tissue around the implant is not damaged by the heat of the eddy currents (implant heating in MRI).

SUMMARY OF THE INVENTION

The above problems are solved particularly well by a metal outer casing part having the features of the first independent claim. Expedient developments of the inventive concept are the subject of the dependent claims. In particular, a feedthrough flange is provided. An implantable, medical electronic device having the features of the second independent claim is also provided.

The invention includes the concept of providing structural cavities preferably in the outer casing wall of the outer casing part of the aforementioned devices, which cavities on the one hand lead to a reduction in weight and on the other hand prevent the flow of eddy currents. Furthermore, the same effect can be achieved by the inclusion of non-conductive substances (for example a gas such as air or inert gas) or non-conductive particles (non-metal, inorganic, for example aluminium oxide, titanium oxide, silicon oxide, glass). These substances or particles preferably have a lower density than the casing material or the casing materials. Furthermore, the invention includes the concept of closing off such cavities and/or non-conductive inclusions towards the intended device outer side and/or device inner side by use of a closed metal layer so that the hermetic seal of the outer casing remains ensured. With this concept, both a saving in weight and also advantageous properties of the device in the event of MRI and similar examinations can be attained without compromising other properties, in particular the long-term reliability.

An inner cavity and/or non-conductive inclusion in a wall is an interior that is enclosed on all sides by the wall of the outer casing, even if the medical device (cardiac pacemaker, defibrillator, nerve stimulator) itself has not yet been joined or assembled in the end state. The cavities and/or non-conductive inclusions must therefore be introduced already inherently in the structural components (flange, housing half-shells). During production, the structural component is manufactured from a base material (for example titanium Grade 1, titanium Grade 2, titanium Grade 4, titanium Grade 5, nitinol, Ti-6Al-4, Ti-6Al-7Nb, Ti-5Al-2,5Fe, Mo, Nb, Pt) and cavities having a gaseous filling (for example atmosphere, argon, helium, hydrogen) and/or insulating particles (for example aluminium oxide, titanium oxide, silicon oxide, tungsten carbide, aluminium nitrite, or the like) introduced into the wall of the component.

The inner cavities preferably have a volume between $5.0 \times 10^{-5}$ mm$^3$ and $5.0 \times 10^{-2}$ mm$^3$ and/or pores with a diameter preferably of 50 μm-500 μm.

In one embodiment of the invention, at least a portion of the outer casing part comprises a plurality of layers connected to one another materially, in particular integrally, wherein at least one inner layer comprises multiple small cavities or particles formed from an insulating material. The layer or layers in principle can be highly porous, i.e. for example can be formed by metal foam. However, they can also contain cavities or insulating bodies introduced locally in a defined manner. Currently, an embodiment with at least one inner layer, which has a regular configuration of small cavities or insulating bodies, is preferred. A further embodiment has an irregular distribution of the cavities or insulating bodies within the outer casing wall.

In a further preferred embodiment the outer casing wall part has a plurality of inner layers arranged one above the other, which have different arrangements of small cavities with different cavity size and/or shape and/or different cavity spacings. The cavities have an extent preferably of from 10 to 500 μm. For example, one of the layers can thus contain a large number of small cavities, a further layer there-above can contain a smaller number of slightly larger cavities, and yet a further layer can contain an even smaller number of even larger cavities, or layers with a greater or smaller number of cavities or with smaller or larger cavities or with cavities arranged more closely together or further distanced from one another are arranged in alternation. The same is true for the multi-layer structures with insulating particles. On the one hand, the static requirements on the device casing can be reliably satisfied and on the other hand the most efficient prevention possible of eddy currents is achieved.

In further embodiments of the invention electrically insulating particles, for example formed from non-metal, inorganic materials (for example ceramic materials), are provided. Ceramic particles with a size of approximately 1-250 μm, which are inserted into metal materials, are particularly advantageous. Particles formed from ceramic material (for example $Al_2O_3$, $SiO_2$) which have a high biocompatibility, a lower density than titanium, and maintain a stable volume, without phase transitions during the production process (sintering, heat treatment, high-temperature soldering, and the like) are well suited.

Production of the outer casing parts can be achieved by all additive manufacturing methods. The production of the components shall be explained by way of example on the basis of screen printing, as described for example in international patent disclosures WO 2014/187567 A2 and WO 1993/016865 A1, corresponding to U.S. patent publication 2016/0121599 and U.S. Pat. No. 5,714,103 respectively).

The production process starts with the manufacture of various screens or stencils. The screens can be stabilized by use of fine wires so that finer structures can be achieved. Areas that will be used later for the application of material are exposed in the screen by photolithography and selective etching. A screen is created for each altered geometry in the direction of construction (perpendicularly to the support).

During the screen printing process, the material to be printed is applied to the screen and distributed over the screen by a doctor blade. Here, each layer height is printed at approximately the screen height. The process is repeated a number of times until the component has been fully constructed. For example in order to produce an outer casing part made of titanium with inner cavities/pore structure, a paste (for example titanium, niobium) is preferably produced for the printing process. Material is applied successively by the doctor blade or by the printing by a plurality of suitably structured screens on a suitable print substrate or on the previously produced layer. Each layer is suitably dried before applying the next layer by means of IR or UV dryer depending on the used binder system. The titanium powder in the print paste can have, for example, a mean particle size in the range between 10 and 30 μm, in particular between 10 and 20 μm, and a screen with a mesh opening for example in the range between 50 and 100 μm and with a wire diameter in the range between 15 and 40 μm can be used. In order to achieve the desired inner cavities, an approach is preferably adopted in which a plurality of individual layers with selective free spaces are created, which are produced by closed screen regions and are then printed over with a screen opened again at these points. It has surprisingly been found that if a paste system having shear thinning properties is used for this purpose, the paste does not fill the created cavities, and instead stretches over them.

A Ti powder having the finest possible grain size (for example 10-45 μm) is particularly preferably used for the Ti basic structure, and powder with coarse grain size (for example 40-150 μm) is particularly preferably used for covering the cavities (exposed prior to the application of the cover layer). Alternatively to the covering of the cavities with coarse powders, the cavities can also be filled with the above-described ceramic powders before being covered which allows a greater dimensioning of the cavities, even for EDM and LBM methods.

Alternatively to cavities, layers having increased insulator content (for example $Al_2O_3$, $SiO_2$, WC) can also be mixed by producing a powder or paste which consists of a metal powder and an insulator.

In order to achieve a mechanical strength necessary for the further processing and/or application, the layer structure is debinded following manufacture in an inert gas atmosphere and is sintered under high vacuum at temperatures >1000° C. Particularly also in view of the subsequent joining process of the outer casing parts, for example by means of laser welding, a minimal oxygen pick-up must be ensured over the entire process chain. Otherwise, the melt zone will become brittle, leading to an undesirable degradation of the mechanical strength over the period of use of the implant.

In further embodiments of the invention at least one layer comprises a different material compared to at least one of the other layers. In particular, at least one inner layer of the layer composite comprises a different material compared to the two layers delimiting the outer casing part outwardly. For example, the outer material (for example titanium Grade 1, 2, 4 or 5, stainless steel 316L) can be selected depending on the requirements of weldability, whereas the material of the inner layers can be selected such that the saving in weight is as high as possible and/or the elimination of eddy currents is as efficient as possible, for example aluminium, copper, titanium Grade 2, and aluminium oxide. However, it is also possible to form the layers substantially of a single material or a base material having relatively minor admixtures.

The proposed outer casing part can also be produced in a technically simple manner as a sintered part, wherein the layers are sintered to one another. The production of parts of this kind forms its own technical field—powder metallurgy—and therefore comprehensive knowledge and fully-developed techniques are available to a person skilled in the art for production of the housing of medical electronic devices, and said person can choose from this knowledge and these techniques as a matter of routine. A more accurate description of the production of this embodiment has therefore been omitted here.

In order to produce the primary component structure in a technically simple manner, the outer casing part is formed in particular as a thermally solidified 3D printed part, which comprises a plurality of layers each formed by printing a metal powder composition. The used printing method specifically, besides the screen printing method already described, can also be an originally generative printing method in the form of jet printing.

Here, printing pastes with various degrees of purity and primary grain structure can be used. Furthermore, the pastes can be added to selectively electrically insulating constituents, which worsen the conductivity of the workpiece locally.

Other features which are considered as characteristic for the invention are set forth in the appended claims.

Although the invention is illustrated and described herein as embodied in an outer casing part of an implantable medical electronic device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIGS. 2A, 2B and 2C show a schematic perspective illustration, a sectional view of an embodiment of an outer casing part according to the invention, and a sequence of steps in various levels of the outer casing part.

DETAILED DESCRIPTION OF THE INVENTION

Figure 1:
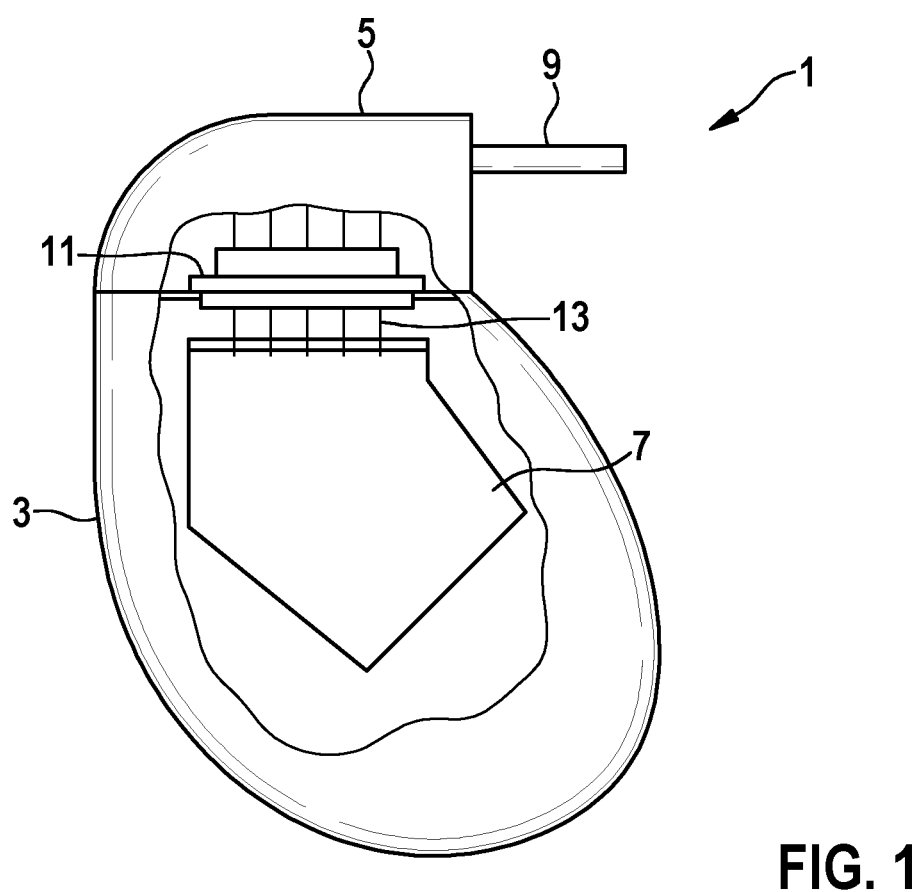
FIG. 1 is a schematic, partially sectional illustration of an implantable medical electronic device.

Referring now to the figures of the drawings in detail and first, particularly to FIG. 1 thereof, there is shown schematically a cardiac pacemaker 1 with a pacemaker housing 3 and a head part (header) 5, in the interior of which, besides other electronic components, there is arranged a printed circuit board (PCB) 7, with an electrode lead 9 connected to the lead connection (not shown) of the PCB 7 arranged in the header. A feedthrough 11 provided between the device housing 3 and header 5 and held in a feedthrough flange 12 comprises a plurality of connection elements 13 for external connection of the printed circuit board 7.

FIGS. 2A, 2B and 2C show schematically a design of an outer casing part denoted here by reference sign 10, which for example can form a portion of the housing 3 or can form a semi-finished product for producing a feedthrough flange of the feedthrough 11 of the cardiac pacemaker 1 shown schematically in FIG. 1 and briefly described above.

Figure 3:
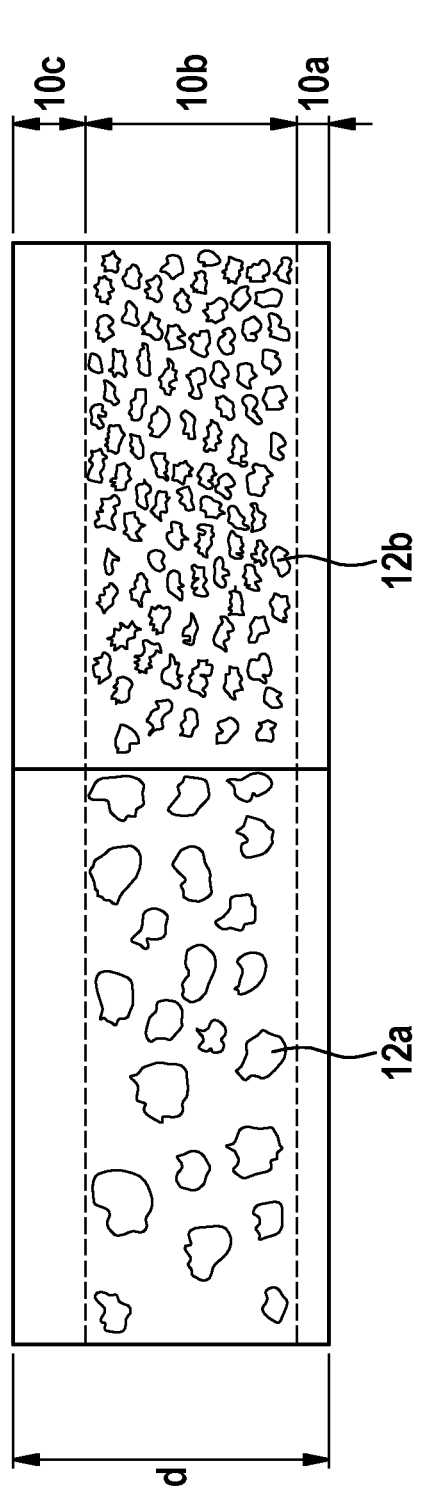
FIG. 3 is a sectional view through a pacemaker housing with supplied particles in a middle region of the outer casing.

FIG. 3 shows schematically a cross-section through the outer casing part 10 of a medical implant, for example a pacemaker. The upper regions 10a and the lower regions 10e are formed from a closed metal layer, for example from titanium Grade 2.

The middle region 10b consists of a metal, for example titanium Grade 3 with embedded insulating ceramic particles 12a and 12b of different sizes, for example formed from $Al_2O_3$.

The outer casing part 10, as already shown in FIG. 2B, has a layered structure formed for example of five layers materially connected to one another, as can be seen more precisely from the longitudinal sectional illustrations of individual layers 10a to 10e in FIG. 2C. Of these, the uppermost layer 10*a* and the lowermost layer 10*e* and a middle layer 10*c* are closed metal layers, whereas the intermediate layers 10*b* and 10*d* each comprise three groups of regularly arranged cavities. The different cavities beneath these layers are to be understood merely as illustrations, and the different arrangement of cavities in the two layers 10*b* and 10*d* is also to be understood merely by way of example. In practice, embodiments in which cavities are distributed over an entire layer with a specific size, shape and specific spacing tend to be used, whereas cavities of a different size, shape and/or with different spacings will be provided in another layer, so as to satisfy stability and electrical requirements determined with regard to the layer composite as a whole. The layer sequences 10*b*, 10*c*, 10*d* can be repeated a number of times in different order before the structure is terminated by 10*a* and 10*e*. As can be seen in 10*b*, honeycomb, circle, rectangle, ball, and cylinder structures are advantageous in particular.

The shown structures of the layers 10*b* and 10*d* can be produced for example by means of a suitably designed screen printing stencil (produced for example by means of photolithography) in a screen printing method or also by appropriate control of a jet printing system. The typical structure size in the described processes is 1-30 μm.

In addition, the invention can also be implemented in a large number of modifications of the example shown here and aspects of the invention discussed further above.

For example, it is conceivable to provide even finer cavity structures as a result of the selective use of finer Ti powders and finer screens.

Alternatively to the technique of screen printing, further additive shaping methods can also be used in order to produce the described structures in the outer casing part, for example injection moulding (MIM, PIN). Here, a granular material having a high material purity is firstly injected in a preliminary manner. The component is then injected to its end state by a second granular material having a content of propellants and/or a ceramic content. During the sintering, the propellant can produce the cavities and the ceramic inclusions are fixedly incorporated in the structure.

Further 3D printing methods (for example inkjet, filament printing) or also SLM or EBM are also possible. However, particularly with use of electron or laser beam processes, it must be ensured that suitable powders are used, which form the titanium basic structure. With the choice of LBM or EBM, however, there can be a limitation of the degrees of freedom in respect of the design of the cavities and size and thickness of the layer covering the cavities.

Lastly, further aspects of the present invention and embodiments of these aspects will be formulated hereinafter as items, wherein these items can also be formulated as claims of the present invention. In particular, the reference signs between parentheses relate to the drawings.

The following is a summary list of corresponding structure used in the above description of the invention:

Item 1: a metal outer casing part 10 of an implantable medical electronic device 1 comprising at least one inner cavity and/or non-conductive inclusion or portion 10*b*, 10*d* with multiple small cavities and/or non-conductive inclusions 12*a*, 12*b*, which is closed off in a hermetically sealed manner at least towards the device outer side by means of a closed metal layer 10*a*, 10*e*.

Item 2: the outer casing part according to item 1, comprising a plurality of layers 10*a*-10*e* materially connected to one another integrally, wherein at least one inner layer 10*b*, 10*d* comprises multiple small cavities and/or non-conductive inclusions 12*a*, 12*b*.

Item 3: the outer casing part according to item 2, wherein the inner layers or at least one inner layer 10*b*, 10*d* are/is formed from foamed metal material.

Item 4: the outer casing part according to item 2, wherein the inner layers or at least one inner layer 10*b*, 10*d* have/has a regular configuration of small cavities.

Item 5: the outer casing part according to any one of item 2 to 4, comprising a plurality of inner layers 10*b*-10*d* arranged one above the other, which have different arrangements of small cavities of different size and/or shape and/or different and/or non-conductive inclusions.

Item 6: the outer casing part according to any one of item 2 to 5, formed as a sintered part 10, in which the layers are sintered to one another.

Item 7: the outer casing part according to any one of item 2 to 6, wherein at least one layer comprises a different material compared to at least one of the other layers.

Item 8: the outer casing part according to item 7, wherein at least one inner layer 10*b*-10*d* comprises a different material compared to the two layers 10*a*, 10*e* outwardly delimiting the outer casing part.

Item 9: the outer casing part according to item 7 or 8, wherein the other material of the at least one layer differs in terms of density and/or conductivity from the material of the other layers.

Item 10: the outer casing part according to any one of the preceding item, formed as a thermally solidified 3D printed part 10, which comprises a plurality of layers 10*a*-10*e* formed by printing a metal powder composition.

Item 11: the outer casing part according to any one of the preceding item, formed as a feedthrough flange 10 with at least one through-opening for a connection element or an insulating body for receiving connection elements in an insulated manner.

Item 12: the outer casing part according to any one of item 1 to 10, formed as a housing half-shell or as part of a housing half-shell 3 of an implantable medical electronic device 1.

Item 13: a medical electronic device 1, in particular a cardiac pacemaker, cardioverter, cochlear implant or neurostimulator with a metal outer casing part 10 according to any one of the preceding item.

The invention claimed is:

1. A metal outer casing part for an implantable medical electronic device, the metal outer casing part comprising:
   a first closed metal layer; and
   an outer casing wall having at least one inner cavity and/or non-conductive inclusion formed and/or disposed therein, said at least one inner cavity and/or non-conductive inclusion is closed off in a hermetically sealed manner at least towards an intended device outer side by means of said first closed metal layer;
   a second closed metal layer, said second closed metal layer, said outer casing wall and said first closed metal layer being vertically stacked in succession.

2. The metal outer casing part according to claim 1, wherein said at least one inner cavity and/or non-conductive inclusion is closed off in a hermetically sealed manner at least towards an intended device inner side by means of said second closed metal layer.

3. The metal outer casing part according to claim 1, wherein said outer casing wall has at least one portion with a plurality of small cavities and/or non-conductive inclusions.

4. The outer casing part according to claim 3, wherein said at least one portion of the outer casing wall has a plurality of layers materially connected to one another integrally, said plurality of layers including at least one inner layer having said plurality of small cavities and/or non-conductive inclusions.

5. The outer casing part according to claim 4, wherein said at least one inner layer is formed from foamed metal material.

6. The outer casing part according to claim 4, wherein said at least one inner layer has a regular configuration of said plurality of small cavities and/or inclusions.

7. The outer casing part according to claim 4, wherein said at least one inner layer is one of a plurality of inner layers disposed one above another and have different arrangements of said plurality of small cavities and/or inclusions of different size and/or shape.

8. The outer casing part according to claim 4, wherein said at least one portion of said outer casing wall is formed as a sintered part, in which said plurality of layers are sintered to one another.

9. The outer casing part according to claim 4, wherein at least one of said plurality of layers has a different material compared to at least one of a rest of said plurality of layers.

10. The outer casing part according to claim 9, wherein said at least one inner layer having a different material compared to said first and second closed metal layers outwardly delimiting the outer casing part.

11. The outer casing part according to claim 9, wherein said different material of said at least one layer differs in terms of density and/or conductivity from a material of the rest of said plurality of layers.

12. The outer casing part according to claim 4, wherein said at least one portion of said outer casing wall is formed as a thermally solidified 3D printed part having said plurality of layers each formed by printing a metal powder composition.

13. The outer casing part according to claim 1, wherein the outer casing part is formed as a feedthrough flange with at least one through-opening formed therein for a connection element or an insulating body for receiving connection elements in an insulated manner.

14. The outer casing part according to claim 1, wherein the outer casing part is formed as a housing half-shell or as part of a housing half-shell of an implantable medical electronic device.

15. The outer casing part according to claim 4, wherein said at least one inner layer is one of a plurality of inner layers formed from a foamed metal material.

16. The outer casing part according to claim 4, wherein said at least one inner layer is one of a plurality of inner layers having a regular configuration of said plurality of small cavities and/or inclusions.

17. A medical electronic device, comprising:
a metal outer casing part containing a first closed metal layer, a second closed metal layer and an outer casing wall having at least one inner cavity and/or non-conductive inclusion formed and/or disposed therein, said at least one inner cavity and/or non-conductive inclusion is closed off in a hermetically sealed manner at least towards an intended device outer side by means of said first closed metal layer, said second closed metal layer, said outer casing wall and said first closed metal layer being vertically stacked in succession.

18. The medical electronic device according to claim 17, wherein the medical electronic device is selected from the group consisting of a cardiac pacemaker, cardioverter, cochlear implant and a neurostimulator.

* * * * *